(12) United States Patent
De Munck et al.

(10) Patent No.: US 8,344,174 B2
(45) Date of Patent: Jan. 1, 2013

(54) BATCH ESTERIFICATION

(75) Inventors: Nicolaas Anthony De Munck, Barendrecht (NL); Klaas Bandstra, Brielle (NL); Raphael Frans Caers, Edegem (BE); Brady Compton, Baton Rouge, LA (US); John Lyford, IV, Baton Rouge, LA (US); Aad Gerrit Oskam, Rozenburg (NL); Berend Jan Van Der Veen, Hellevoetsluis (NL)

(73) Assignee: ExxonMobil Chemical Patents Inc., Houston, TX (US)

( * ) Notice: Subject to any disclaimer, the term of this patent is extended or adjusted under 35 U.S.C. 154(b) by 431 days.

(21) Appl. No.: 12/527,048

(22) PCT Filed: Mar. 7, 2008

(86) PCT No.: PCT/EP2008/001838
§ 371 (c)(1),
(2), (4) Date: Nov. 17, 2009

(87) PCT Pub. No.: WO2008/110306
PCT Pub. Date: Sep. 18, 2008

(65) Prior Publication Data
US 2010/0137631 A1 Jun. 3, 2010

Related U.S. Application Data

(60) Provisional application No. 60/906,797, filed on Mar. 13, 2007.

(51) Int. Cl.
*C07C 67/08* (2006.01)
(52) U.S. Cl. .......................................... 560/98; 560/99
(58) Field of Classification Search .................. 560/98, 560/99
See application file for complete search history.

(56) References Cited

U.S. PATENT DOCUMENTS

| 2,459,014 | A | 1/1949 | Cavanaugh et al. |
| 5,349,075 | A | 9/1994 | van den Berg et al. |
| 5,866,710 | A | 2/1999 | Ridland et al. |
| 6,284,917 | B1 | 9/2001 | Brunner et al. |
| 6,355,817 | B1 * | 3/2002 | Woods et al. ................ 554/170 |
| 6,888,021 | B2 | 5/2005 | Brunner et al. |
| 2002/0028963 | A1 | 3/2002 | Gubisch et al. |

FOREIGN PATENT DOCUMENTS

| EP | 0 434 390 | 6/1991 |
| EP | 1 186 593 | 3/2002 |
| EP | 1 300 388 | 4/2003 |
| EP | 1 719 753 | 11/2006 |
| EP | 1719753 | 11/2006 |
| FR | 1 269 888 | 8/1961 |
| GB | 777628 | 6/1957 |
| GB | 1076702 | 7/1967 |
| GB | 1 426 057 | 2/1976 |
| WO | 99/41226 | 8/1999 |
| WO | WO99/41226 | 8/1999 |

OTHER PUBLICATIONS

Kirk-Othmer Encyclopaedia of Chemical Technology, Fourth Edition (1994), vol. 9, pp. 762-768.
DuPont Performance Chemicals: "TYZOR® Titanates as Catalysts for Plasticizer Production,"(DuPont Sales Brochure; Claim Publication Date by Evonik Industries, Jun. 26, 2000), pp. 1-16.

* cited by examiner

*Primary Examiner* — Yong Chu
(74) *Attorney, Agent, or Firm* — Andrew B. Griffis; Leandro Arechederra, III

(57) ABSTRACT

The efficiency of catalyzed batch esterification reactions is improved by the use of a particular temperature and pressure profile during the reaction cycle. In particular elevated pressure is maintained to prevent alcohol boil off during initial mixing and reaction of the reactants prior to any catalyst addition, and preferably the pressure is reduced rapidly after the desired reaction temperature has been reached.

18 Claims, 2 Drawing Sheets

BATCH ESTERIFICATION

CROSS REFERENCE TO RELATED APPLICATIONS

This application is a 371 National Stage Application of International Application No. PCT/EP2008/001838, filed Mar. 7, 2008, which claims the benefit of Provisional Application No. 60/906,797, filed Mar. 13, 2007, the disclosures of which are herein incorporated by reference in their entireties.

FIELD OF THE INVENTION

The present invention relates to batch processes for the catalysed production of esters, primarily from alcohols and acids or anhydrides, primarily carboxylic acids or their anhydrides. More particularly but not exclusively, the invention is directed to an improved process for preparing plasticizer esters for polyvinylchloride (PVC), such as benzoates, phthalates, cyclohexanoates, cyclohexanoic dicarboxylic esters, adipates and trimellitates. In a preferred embodiment, the esterification is performed in the presence of an esterification catalyst such as a titanium, zirconium, or tin-based organometallic catalysts. The invention is also useful for preparing esters of polyols and carboxylic acids.

BACKGROUND OF THE INVENTION

Esters are most commonly prepared by the reaction of an acid and an alcohol accompanied by the elimination of water. Esters may also be formed by reaction of an alcohol with various other reactants including acid anhydrides, acid chlorides, amides, nitriles, aldehydes, and ketones. Mixtures of acids and/or alcohols may also be used as starting materials. The same may apply for the other reactants.

The reaction conditions under which esterification is effected, can be varied considerably. The reaction proceeds very slowly at room temperature, but quite rapidly at elevated temperatures. Typically one of the reactants is used in stoichiometric excess in order to drive the reaction. The other reactant is then called the limiting reagent. About 99% of the limiting reagent, e.g., acids, anhydrides, alcohols or polyols, can be converted to an ester within a few hours. Limiting reagents are typically reagents which are not present in stoichiometric excess, e.g., limiting reagents used to make plasticizers include diacids and phthalic anhydride and those used to make polyol esters are polyols.

Because the esterification of an alcohol and an organic acid or anhydride is a reversible reaction, the esterification reaction normally does not go to completion. However, conversions of over 99% can be achieved by removing at least one of the esterification products, typically water. If one of the products is boiling at a lower temperature than the other one and than the reagents, this removal is typically achieved by distillation. A variety of distillation techniques are known in the art to remove the produced water from the reaction zone. One method of water removal includes carrying out the reaction in a liquid medium which may form an azeotrope having a boiling point that is lower than that of either or each component of the reaction. If the reagents and the resulting ester have boiling points above 100° C. at atmospheric pressure, then the reaction temperature can be adjusted such that no liquid medium capable of forming an azeotrope with water is required. Additionally, an entrainer may be used to aid in the distillation of the water from the reaction mixture. Inert materials such as cyclohexane, hexane, benzene, toluene, or xylene may be used as an entrainer in the production of phthalate esters. In addition, the reactant having the lower boiling point may also be employed as the entrainer. In this latter case, the reactant used as the entrainer is typically charged into the reaction mixture in excess over the stoichiometric quantities required for the reaction. Esterification processes, including those employing water removal, may be conducted in a batch or continuous mode of operation. Various esterification processes are disclosed in Volume 9 of the Kirk-Othmer Encyclopaedia of Chemical Technology, Fourth Edition (1994), pp. 762-768, the entirety of which is hereby incorporated by reference.

A conventional batch esterification procedure includes charging all of the reactants into the reactor at the beginning of the reaction cycle. In catalytic esterification processes, the catalyst is typically added to the reaction mixture after the batch reaches a target temperature. The reaction mixture may then be heated further. The temperature of the reaction mixture rises until the boiling point of the reaction mixture is achieved, at which point the entrainer, if used, and water by-product boil out of the reaction mixture. Typically, the overhead vapours are condensed, the water separated from the entrainer, and the entrainer recycled to the reactor vessel. The reaction temperature, and therefore the rate of reaction, is limited by the boiling point of the reaction mixture. When the reactant with the lower boiling point is also used as the entrainer, its concentration is gradually reduced as the reaction proceeds. Also the concentrations of the reactants decrease during the reaction, which negatively affects the reaction rate. Thus the reaction temperature, and, therefore, the rate constant for the reaction, increases as the reaction proceeds, irrespective whether an entrainer is used or not, particularly if heat input is continued during the course of the reaction.

One conventional process for forming plasticizer esters is disclosed in UK Patent 1,426,057 (Imperial Chemical Industries Limited), wherein plasticizer esters are prepared from phthalic anhydride and a $C_4$ to $C_{14}$ alkanol or mixture of such alkanols. For example, a mixture of phthalic anhydride and one or more of these alkanols may be heated gradually up to 180 to 260° C. in the presence of a titanium catalyst (e.g., titanium isopropoxide). When the temperature reaches 180 to 260° C., the esterification is substantially complete although the residual acidity is about 0.3 to 0.05 mg KOH/gram. Aqueous sodium carbonate solution is then slowly added to the ester product to provide 1 to 12 times the stoichiometric amount of alkali. When the temperature has fallen to between 150 and 200° C., water or a dilute aqueous alkali solution is admitted and the excess alkanol is removed. By this treatment, the titanium catalyst is converted to titanium oxide and precipitated, and, thereafter, may be filtered off with excess sodium carbonate and the residual acidity is reduced to less than 0.05 mg KOH/gram.

Conventional esterification processes may be accomplished in two reaction steps. The first reaction step generally occurs in the absence of an esterification catalyst, while the second reaction step may include the use of an esterification catalyst. In U.S. Pat. No. 5,349,075 to Van den Berg et al. a two step esterification process with a first uncatalyzed esterification reaction step conducted at a temperature of at least 200° C., i.e. conditions whereby the more volatile reactant is in the gaseous phase while the less volatile reactant is in the liquid phase, followed by a catalyzed second esterification reaction step at a temperature below 100° C. is proposed. The process employs a solid acid catalyst in the second reaction step.

In the commercial production of plasticizer esters, e.g. phthalates, adipates, and trimellitates, conversions of greater than 99% are desired. For polyol esters, e.g. esters made from aliphatic acids and trimethylolpropane (i.e., the limiting reagent), the commercially desirable conversions are at greater than 98%. Typical polyol ester product applications require conversions of about 98.5% of the original number of hydroxyl groups in the poly alcohol, though applications for products with partial conversion of the hydroxyl groups, such as about 35% unconverted hydroxyl groups, are also known.

Most esterification processes are capable of converting about 99% of the limiting reagent, such as acids, anhydrides or polyols, to an ester within a few hours of reaction time; however, after about 90% of the limiting reagent is converted, the rate of reaction tends to slow down substantially. It may take half as long again to convert the remaining 4-5% of limiting reagent as it took to convert the initial 95% thereof.

The chemical industry is continuously seeking to decrease the reaction time or the batch cycle time of esterification, as well as the quality of the resultant esters. It would therefore be desirable to develop a process which increases the overall rate of reaction especially during the early part of the reaction or of the batch cycle.

The esterification of dibasic acids or acid anhydrides proceeds by the first esterification of one acid group or partial esterification of the anhydride in both instances resulting in the formation of a mono-ester. In this first reaction a catalyst may not be required. Subsequently the esterification is completed to form the di-ester, generally in the presence of a catalyst. The catalytic esterification is typically performed by mixing the dibasic acid or anhydride and the alcohol, and raising the temperature to a certain level at which the catalyst is added. Since at least the formation of the mono-ester is a substantially instantaneous reaction when an anhydride is involved, and otherwise still a faster reaction than the second step, a significant amount of esterification therefore may already occur before the addition of catalyst, whose presence is desired or even required to drive the reaction to completion in a commercially acceptable time.

The esterification reaction produces water and since the titanium or tin esterification catalysts that are typically used are water sensitive, it is necessary to minimize contact between the water produced in the reaction and the catalyst. Accordingly it has been practice to distil off as much as possible of any water of reaction during the initial phases of the reaction, prior to addition of the catalyst. Thus in a typical reaction such as that described in U.S. Pat. No. 6,355,817 B1, a dialkyl phthalate was produced by reacting phthalic anhydride and an alcohol under reduced pressure to maintain a constant boil up of the reaction mixture. However this process requires a relatively long cycle time and also involves boiling off and recycle of reactants, particularly the alcohol. Generally the alcohol is recycled by reflux, which is typically subcooled and can therefore lower the temperature of the reaction mixture and further prolong the reaction cycle time, in particular when heat input capabilities are limited, which is usually the case in an industrial setting.

There remains therefore a need to improve the production of such reactions, to reduce batch cycle times, to improve catalyst use and to generally improve the overall efficiency of the reaction including optimisation of the use of the heat supplied to the reaction. We have now found that the efficiency of the reaction may be significantly improved by the use of a particular temperature and pressure profile during the reaction, and particularly during the initial stages of the reaction.

SUMMARY OF THE INVENTION

Accordingly the present invention provides a process for the catalysed esterification of reactants comprising an acid or anhydride and an alcohol, which process comprises a batch reaction sequence that comprises (i) providing a mixture of the acid or acid anhydride with the alcohol at an initial temperature in a reaction vessel,
(ii) raising the temperature of the mixture to a desired esterification reaction temperature to effect esterification, and
(iii) boiling off water by-product produced in the esterification reaction, wherein the pressure in the reaction vessel is elevated as the temperature of the mixture is raised during at least the initial phase of raising the temperature of the mixture, thereby reducing reactant vaporisation, and the esterification catalyst is introduced into the mixture at a predetermined mixture temperature that is below the desired esterification reaction temperature and above the initial temperature of the mixture.

The process of the invention is particularly suitable to produce a plasticizer ester from a $C_4$ to $C_{15}$ monohydric alcohol or a polyol ester from a polyol and a fatty acid.

DETAILED DESCRIPTION OF THE INVENTION

The temperature of the mixture ("mixture temperature") when the catalyst is introduced is determined by the operator to suit the system employed. For convenience, this temperature is designated the "predetermined mixture temperature". The terms "predetermined mixture temperature", "desired esterification reaction temperature", and "initial temperature of the mixture" are used herein to indicate temperatures within temperature ranges that are known to be appropriate for a particular catalysed esterification reaction. For example the desired esterification reaction temperature and predetermined mixture temperature will vary according to the nature of the reactants and the nature of the catalyst, and the invention does not concern these particular conditions but is concerned with the conditions that should be used depending on these particular temperature conditions which are well known according to the reactants and catalyst employed.

We have found that increasing the pressure in this manner ensures that the heat supplied to the reaction mixture is used for heating the reactants, rather than for vaporisation of the reactants. Within heat input limited equipment, this minimizes the time to reach the minimum desired temperature for the esterification reaction, which assures maximum achievable reaction rate. This in turn enables a reduction in reaction cycle time. In addition, the increased pressure and reduced vaporisation rate allow the predetermined mixture temperature, at which the catalyst is introduced, to be reached sooner, thereby further reducing the reaction time. Furthermore, since, during this initial stage of the reaction vaporisation of the reactants, particularly of alcohol, is substantially reduced, there is no requirement for reflux, thus avoiding the extra cooling effect of the refluxed material. This again enables better use of the heat supplied and also allows the predetermined mixture temperature to be reached sooner, thereby further reducing the reactor cycle time. Less alcohol in the vapour phase and in the overhead reflux system also means more alcohol in the reactant liquid mixture, which by its higher alcohol concentration assures a higher reaction rate again.

The catalyst should be added after the mixing of the acid or anhydride and the alcohol or polyol and at a predetermined mixture temperature above the initial temperature of the mixture. The elevated pressure is preferably maintained at least until the catalyst is added. In a preferred embodiment, the catalyst is added to the mixture when it is at a temperature in the range 175° C. to 220° C.

The catalyst is generally added at a temperature below the desired esterification reaction temperature and, accordingly, after catalyst addition the temperature of the mixture is increased further to the desired esterification reaction temperature. Although the catalyst activity increases with increasing temperature, its stability decreases with increasing temperature and accordingly, depending on the nature of the catalyst, there is an optimum reaction temperature or a fairly narrow optimal temperature range. Irrespective of this temperature or range, addition of the catalyst causes the formation of more water at a faster rate, which must be removed rapidly so that, with titanate catalyst, it has less chance of hydrolysing the water-sensitive catalyst. Accordingly, in a preferred embodiment of the present invention, after the addition of the catalyst and reaching the desired esterification reaction temperature or the lower end of the optimal range, the pressure is reduced rapidly, preferably to atmospheric pressure, and more preferably to below atmospheric, to cause the water to vaporise whilst the reaction temperature is at least maintained at the desired esterification reaction temperature or the lower end of the optimal range, but preferably increased further to ultimately reach the maximum desired esterification reaction temperature.

In another embodiment the invention therefore provides an esterification process in which
i) an acid or acid anhydride and an alcohol or polyol reactants are introduced and mixed in the reaction vessel, and the mixture is heated to a temperature below the boil up temperature of any of the reactants;
ii) the reaction mixture is heated further while the reactor pressure is raised such that reaction water is allowed to vaporise but boil up of any of the reactants is essentially avoided;
iii) catalyst is added at a predetermined mixture temperature;
iv) the temperature of the mixture is increased to the minimum desired esterification reaction temperature;
v) after the minimum desired esterification reaction temperature is reached, the reactor pressure is reduced while at least maintaining the minimum desired esterification reaction temperature.

Preferably the pressure is reduced in (v) rapidly, e.g. in a time period of 2-20 minutes, typically about 8-10 minutes, down to atmospheric pressure. Ideally the pressure is reduced as fast as the equipment capabilities and operating and safety considerations allow, because more important than reducing the pressure fast is to maintain the temperature of the reacting mixture at least the minimum desired esterification reaction temperature, and preferably even to increase the mixture temperature to the maximum desired esterification reaction temperature. Ideally the pressure should have reached atmospheric pressure by the time the mixture temperature reaches this maximum desired esterification reaction temperature. After reaching atmospheric pressure, the pressure is preferably further reduced by pulling vacuum on the reactor. It is preferred to further reduce the pressure rapidly, because the faster this happens, the higher the rate of water removal is. The pressure reduction rate however remains conditional on maintaining the temperature of the reaction mixture, as explained below.

One or more of the starting materials, comprising the acid or acid anhydride, the alcohol or polyol, and any recycle of the excess reactant, may be preheated before being mixed with the other reactant or before being introduced into the reaction vessel, such as up to a temperature of 100° C. to 160° C. Oxygen may be removed from one or more of them, preferably from at least one of the fresh starting materials, to improve ester product colour. This oxygen removal occurs preferably after preheating and preferably by nitrogen stripping if it concerns a liquid, or by nitrogen purging of the equipment if it concerns a solid. These pretreatments are preferably performed in a separate vessel, before the starting material is introduced into the reactor vessel. The preheating reduces the reaction batch time, and performing the preheating and/or the oxygen removal in a separate vessel further reduces the time that a particular batch occupies the reactor and therefore also the overall reaction batch time.

Preferably the pressure is reduced to within the range of 1800 mbara (180 kPa) to 300 mbara (30 kPa) within 100 minutes of the addition of the catalyst. This reduction in pressure will however result in the vaporisation of some of the residual unreacted reactants, such as the alcohol, and accordingly it is preferred to introduce reflux conditions at least as soon as at this stage. It is preferred that the reflux system includes a condenser, a reflux drier column (i.e. a tower or column wherein the water content of the reflux is reduced), and/or a flashing step, which is preferably heated, to minimise the water content of the refluxed materials.

The preferred further temperature and pressure profile depends upon the nature of the reactants and the relative quantities. However we prefer that, when titanium catalysis is used, this is the part of the reaction pressure-temperature profile where reaction temperature should be above a minimum desired esterification reaction temperature of 210° C. and preferentially as close as possible to the 220° C. upper limit for titanium catalyst activity and stability, while the control setpoint on reactor pressure is pushed down to enable rapid removal of vapours whilst maintaining the temperature, the speed of which is dependent on the heat input capabilities. If the reaction temperature declines away from its target, the pressure setpoint reduction slope may be temporarily overridden to allow the temperature to regain its previous level, after which the pressure setpoint is again allowed to drop. The temperature decline that triggers the control override is product grade dependent, but is typically no more than 2 degrees Celsius, preferably no more than 1 degree Celsius. The profile of the pressure setpoint is also dependent on the amount of catalyst that is dosed into the reactor.

A variety of heating means may be applied to the esterification reactor to provide heat input. In many processes, the heat input capabilities are a significant limiting factor in shortening the reaction time and hence improving the equipment productivity. Many processes provide heat input by circulating a heating medium through one or more heating coils provided in the reactor, preferably under the liquid level, and/or through a heating mantle around the reactor wall. We have found that steam heating is more effective in transferring heat than hot oil, and we therefore prefer to provide heat input by steam, which preferably is at a pressure sufficiently high that it condenses at a temperature above the temperature of the reaction mixture. We prefer to use high pressure steam at a pressure of at least 40 barg (about 600 psig).

We have found that, by applying and maintaining the pressure above atmospheric during the initial phase of the esterification reaction, water can be removed without the significant alcohol boil off that occurs in known processes which operate at atmospheric or reduced pressure in this initial phase. The use of the higher pressure reduces the need for alcohol recapture and recycle and hence increases the efficiency of the reaction. The use of increased pressure also maximises the usefulness of the heat supply into heating the reaction mixture, and results in the optimum reaction temperature being reached in a shorter time. It also keeps the reactant concentrations in the reaction mixture at the highest possible level. Both these factors result in a faster reaction rate.

The increased pressure also maintains the alcohol level and reduces the water level in the reaction mixture at the time that the catalyst is added and thus reduces the risk of the water damaging the catalyst. The reduction in pressure after the desired esterification reaction temperature is reached and at a time when much of the alcohol has reacted with the acid or anhydride, enables any water still present or being generated to be removed rapidly and where a rapid reduction in pressure is employed, the water will be flashed off. The fact that much of the alcohol has reacted by this stage means that smaller amounts of alcohol will be vaporised, hence requiring less reflux.

The esterification is preferably performed initially under a blanket of inert gas such as nitrogen or methane. The pressure within the reactor, before any vapour vent is opened or vacuum system is commissioned, therefore depends upon the pressure exerted by the inert gas combined with that exerted by the vapours within the reactor, which in turn depends upon the degree of reaction and the extent to which the reactants and the products of the reaction are vaporised, which in turn depends upon the temperature of the reaction. The temperature and therefore the pressure also depends upon the extent to which materials are refluxed. It is therefore preferred that the reactor system be provided with a vent valve and also a gas supply whereby gas may be introduced to increase the pressure within the reactor.

As reactor temperature and pressure increase, a vapour cloud of condensibles, i.e. primarily water but accompanied by some of the lighter boiling reactant, develops above the reactor liquid and displaces the inert gas that filled the reactor initially. The inert gas is pushed into the overhead system, and at a certain moment, the vapour cloud of condensibles reaches the reactor overhead condensor. At that time condensation typically starts, and liquids collect in the overhead separator. Depending on the initial liquid level in the overhead separator, sooner or later the liquid will overflow and the reflux of lighter boiling reactant to the reactor may be activated. We have found there is a tendency for the temperature of the reaction mixture to drop once the reflux system is activated. This in turn leads to a reduction in the pressure within the reactor. We have found that it may be particularly beneficial to introduce uncondensible gas into the reactor at this time to bring the pressure back up to at least re-establishing the desired conditions.

The vent and the gas supply may be provided at any suitable position in the reactor system which typically comprises reactant feed means, a reactor provided with heating means, a condenser, means for the separation of condensed materials, means for the recycle of reactants and means for reaction product removal. The vent and the gas supply may be provided in the reactor or elsewhere and we prefer that they are provided at or close to the condenser, where it is most effective in impairing or stopping condensation which is typically still undesired at that time.

The reactor system is also provided with means for the introduction of the catalyst into the reaction mixture, preferably introducing the catalyst below the surface of the reaction mixture. The means must be such that the catalyst can be introduced into the reactor when it is under superatmospheric pressure. It is therefore preferred that the catalyst be injected into the reactor by means of pressure of the inert gas that is used as the blanket for the reaction. It is also preferred that after the catalyst is injected, the catalyst injection system be flushed with at least one of the reactants. In particular where the esterification comprises the reaction of an acid or anhydride with an alcohol, we prefer that the catalyst injector be flushed with the alcohol. When the catalyst is water sensitive, such as with titanium catalyst, it is preferred that the reactant used for flushing has a low water content, such as at most 500 ppm by weight, preferably at most 200 ppm by weight, most preferably at most 100 ppm by weight.

The reactor is preferably provided with a mixer and, in the preferred reaction cycle, the fresh alcohol feed is introduced into the reactor until a minimum level is reached at which the mixer may be activated. At this stage, the mixer is activated and introduction of the acid or anhydride is instigated; further alcohol consisting of fresh alcohol or recycle alcohol may also be introduced. Reactor heating may be implemented at this time, preferably as soon as the liquid level in the reactor reaches the surface of the heating equipment.

The techniques of the present invention are particularly useful when used in combination with other techniques that are known for improving the efficiency of esterification reactions. In particular the techniques of the present invention may be used with other techniques that are known for minimising contact between water and the esterification catalyst. For example the reaction system may include a reflux drier column, such as is described in U.S. Pat. No. 5,324,853 to L. O. Jones et al. A reflux column or drier serves to heat and dry the condensed alcohol as it is being refluxed for recycle to the reaction. As an alternative, the cold condensed alcohol from the overhead collector may be heated and flashed to remove most of the water as vapor, and the flashed liquid may then be refluxed to the reactor, optionally routed through a reflux drier column to achieve even lower water levels. Another valuable technique is described in European Patent 812818 in which the catalyst is introduced into the reaction mixture below the surface of the liquid reaction mixture. This may be accomplished by the injection of the catalyst through a probe whose opening is below the surface of the liquid reaction mixture. In this way contact between the catalyst and any water rich vapour in the atmosphere above the liquid reaction mixture can be minimised and the catalyst stability preserved.

We have found that reflux drying improves reaction batch time because of the lower water content and the higher temperature of the reflux. This reduces the amount of heat required to revaporise the water in the reflux, and required to heat the colder reflux up to the reaction temperature. We have also found that a larger size reflux drier column allows a steeper pressure profile due to the lower pressure drop in the vapor flowing to the reactor overhead system. We have also found that, in case the reflux drier column cross section is causing an excessive pressure drop, a partial vapor bypass over the drier column may alleviate this problem and help reaching higher reactor productivities, whilst the reflux continues to be adequately dried.

We prefer that esterification processes according to the present invention be performed in the manner described in our copending US patent application Ser. No. 60/906732 (applicant's reference PM2004-064) wherein the esterification recipe and the feed pretreatment are optimised in order to optimise the reaction rate and to reduce reaction time. A particularly preferred reaction cycle for the production of esters and in particular plasticiser esters comprises this feed recipe adjustment and pretreatment followed by the employment of the reaction process of the present invention, followed by the neutralisation technique of WO2006/125670 and the purification techniques of WO2005/021482.

As used herein and in the claims, the term "ester" is used to refer to organic esters, including mono-esters, di-esters, tri-esters, and more generally multi-esters. The term "anhydride" is used to refer to organic anhydrides, including mono-anhydrides, di-anhydrides, and other multi-anhydrides. The term "carboxylic acid" is used to refer to mono-carboxylic acids, di-carboxylic acids, and other multi-carboxylic acids. The term "alcohol" is used to refer to any organic alcohol, including monohydric alcohols, dihydric alcohols, and polyhydric alcohols (polyols) generally.

The preferred cycle of the present invention depends upon the nature of the reactants and the catalyst. A preferred embodiment of the present invention is the esterification of carboxylic acids with alcohols and in particular the esterification of polycarboxylic acids or their anhydrides especially the production of phthalate esters, trimellitate esters and adipate esters. In the preferred cycle, alcohol is preheated to a temperature in the range 100° C. to 160° C. This preferred preheating temperature is grade dependent, because of the change in boiling point. Excessive preheating is to be avoided in order to keep alcohol vapor losses from the preheating step within acceptable limits. For C7 alcohol we prefer to preheat to 100-115° C., for C9 and C10 alcohol we prefer 130-150° C., and for C11 or higher, such as isotridecyl alcohol, we prefer 130-155 or even 160° C. The preheated alcohol is then preferably added to a reaction vessel that is blanketed with an inert gas preferably nitrogen or methane and is heated at a temperature in the range 120° to 150 or 160° C. and is at atmospheric pressure. Maximum heat input to the reactor is preferably applied as soon as possible. The acid or acid anhydride is then added at a temperature in the range 135° C. to 160 or even up to 180° C. The content of the reaction vessel is then rapidly heated to the predetermined mixture temperature at which the catalyst is added. As the contents of the reactor increases, the pressure will increase by compression of the inert gas in the reactor. The pressure will also increase due to vaporisation of some of the reactants and products of reaction, forming a vapour cloud of condensibles above the reactor liquid. The predetermined mixture temperature depends upon the nature of the catalyst and the reactants but is typically in the range 175° C. to 220° C. When this temperature is reached, the catalyst is introduced. The temperature is then further increased to the desired esterification reaction temperature, typically in the range 210° C. to 230° C., with continuing increase in pressure due to the vaporisation of materials. As the vapour cloud of condensibles reaches the condensor, condensation starts and soon thereafter the reflux system is activated. Preferably at that moment, additional inert gas may be provided if required to restore the pressure and to minimise condensation and reflux of reactant to the reactor, as well as the vaporisation from the reacting liquid mixture.

In the production of phthalate esters excess of alcohol over phthalic anhydride is typically used, the preferred molar excess ratios are dependent on the grade of phthalate di-ester being produced. For di-isoheptyl phthalate (DIHP), we prefer to work with an excess of 30%, for di-isononyl phthalate (DINP) we prefer to work with 28% excess, and for di-isodecyl phthalate (DIDP) and for di-isoundecyl phthalate (DIUP) we prefer to use 26.5% excess. We prefer not to deviate more than 0.5% upwards from this preferred level, because this ensures fewer swings and smaller deviations from optimal in the pressure-temperature profile once the reaction temperature has reached its minimum desired level of 210° C. As previously mentioned, this is the part of the reaction pressure-temperature profile where the reaction temperature should be as close as possible to the 220° C. upper limit for titanium catalyst activity and stability, while the control setpoint on reactor pressure is pushed down to enable rapid removal of vapours whilst maintaining the temperature, the speed of which is dependent on the heat input capabilities. If the reaction temperature declines away from its target, the pressure setpoint reduction slope may be temporarily overridden to allow the temperature to regain its previous level, after which the pressure setpoint is again allowed to drop. The temperature decline that triggers the override is grade dependent but is typically no more than 2 degrees C., preferably no more than 1 degree C.

When the desired esterification reaction temperature or range is reached, the pressure in the reaction vessel is preferably rapidly reduced to below atmospheric pressure, while the temperature is at least maintained at the minimum desired esterification reaction temperature. This rapid reduction in pressure may be accomplished by opening the vent valve and/or by pulling vacuum on the reactor using a steam jet, an air jet, or a vacuum pump. Water and the unreacted excess reagent (typically the alcohol in the preferred embodiment) will vaporise, pass to the condenser where they will be condensed and separated. The unreacted reagent may then be recycled to the reactor preferably passing through a reflux column and/or other drier and/or heating step prior to re-entering the reactor.

The invention therefore forms esters by the liquid phase reaction of a carboxylic acid compound and an alcohol. The invention is particularly concerned with the production of plasticizer esters which may be formed by reacting an acid anhydride with at least one alcohol. See Volume A20 of Ullman's Encyclopaedia of Industrial Chemistry, Fifth Edition (1992) pp. 193-196. The reaction is preferably conducted using a 5 to 30 molar % excess of alcohol. More preferably, a 15 to 30 molar % excess of alcohol is used. This invention, while applicable to the catalyzed production of esters generally, is particularly applicable to the production of phthalates, cyclohexanoates, cyclohexanoic dicarboxylic esters, adipates, and trimellitates. This general scheme is also applicable to the production of polyol esters where the acid instead of the alcohol is preferably used in at least stoichiometric amounts and preferably in excess.

The ester molecules produced using the process of the invention may comprise aromatic rings, such as alkyl benzoates, di-alkyl phthalates or tri-alkyl trimellitates. The aromatic rings in these ester molecules may be hydrogenated to produce the corresponding cyclohexane equivalents, such as mono-alkyl, di-alkyl or tri-alkyl cyclohexanoates. In particular, DINP may be further hydrogenated to form di-isononyl di-cyclohexanoate (DINDCH). The process of the invention may therefore be for the production of a phthalate di-ester, in particular DINP, and further comprise the hydrogenation of the phthalate di-ester to the corresponding di-cyclohexanoate, in particular DINDCH. Suitable hydrogenation processes are disclosed in EP 1042273, US 2004/0260113 or WO 2004/046078.

Until the desired esterification reaction temperature is reached, the pressure of the reaction vessel should be maintained at a level sufficient to distil off the water whilst preventing significant alcohol boiling, while forming an ester from the reactants. The pressure of the reaction vessel is generally adjusted continually to ensure continuous vaporisation and removal of water. Typically, the initial reaction pressure is close to atmospheric pressure, for example 1 to 2 bara (101.3 to 202.6 kPa), and moves through a maximum, when the desired esterification reaction temperature or the lower end of the optimal range is reached, of for example 1.5 to 2.5 bara (152.0 to 253.2 kPa), and then reduces toward an increasing vacuum as the reaction proceeds. Preferably, the final reaction pressure ranges from 2 bara (202.6 kPa) to 100 mm Hg absolute (13.3 kPa). More preferably, the final reaction pressure ranges from 1.0 bara (101.3 kPa) to 150 mm Hg absolute (20 kPa). Most preferably, the final reaction pressure ranges from 190 mm Hg absolute (25 kPa) to 350 mm Hg absolute (46.7 kPa), typically 30-31 kPa.

The total amount of catalyst that should be used in the process of the current invention is determined primarily by four factors. First, the total reaction rate generally increases as the amount of catalyst, typically expressed in weight percent of catalyst per weight of limiting reactant, increases up to a certain optimal concentration. The reaction rate also depends on the particular catalyst activity, the reaction temperature and the water content of the reaction mixture. A relatively high concentration of catalyst may result in the organometallic complex esterification catalyst reacting with itself, to form unreactive agglomerated catalyst. Furthermore, a relatively higher concentration of certain esterification catalysts can cause product haze formation. In addition, process economics dictate that beyond an optimal point, further catalyst addition is not economical. If the reaction mixture contains an appreciable amount of certain cationic species, then the catalyst requirement must be increased to reach a desired reaction rate. The amount of catalyst used will therefore be chosen having taken all these factors into consideration.

We have found that, in particular when no reflux drying is performed but even when a reflux drier and/or flash step is provided, stopping the reflux to the reactor before the end of the run is reached, drives the reaction faster to completion because absolutely no more water is returned to the reactor and at the same time the amount of excess reagent in the crude ester is reduced, such as down to 12-15% wt, thereby reducing the volume of crude ester to be further processed and the amount of excess reagent that needs to be removed in the downstream finishing steps. We therefore prefer to stop the reflux at least 2 minutes, preferably at least 5 minutes, more preferably at least 7 minutes and even more preferably at least 10 minutes and even 15 minutes before the expected batch termination time. We have found that when the alcohol reflux is continued till the end of the batch and through a reflux drier, the water content of the crude ester at the end of the reactor run may still be as high as 50 ppm wt. When stopping the alcohol reflux about 12 minutes before the end of the batch termination time, the water content of the crude ester may be only 20 ppm by weight, or may even reach 10 ppm wt or below. We have found that the presence of water, even in these small amounts, may have a surprisingly large effect on the rate of the reaction at the end of run, and therefore on the completion of the reaction and on the total batch time.

When the reflux to the reactor, or to the reflux drying step, is stopped, the alcohol coming from the overhead collection drum is routed to the recycle alcohol tank. When the batch is to be terminated, heat input to the reactor is stopped and the vacuum is broken, preferably by allowing nitrogen into the reactor system, more preferably into the reactor overhead system. This breaking of the vacuum is considered the moment of termination of the batch. As soon as the vacuum is broken, the reactor content may immediately be evacuated to a collection vessel in and from which it may be further processed. In case the next batch of product is of the same quality, the reactor is then ready for starting the new batch.

The process of the present invention can be used to convert polyols and acids to polyol esters. Polyols are organic alcohols, which contain two or more hydroxyl groups. The polyol ester process typically comprises the steps of esterification of the starting carbonyl-like compound with a polyol and a catalyst. In this instance the carbonyl-like compound, or mixture of carbonyl-like compounds, is added to the reaction mixture in stages, such that it is always present in an amount of at least about 5% of the stoichiometric requirements of the total of carbonyl-like compound required to react with the polyol. Preferably, a carboxylic acid is used as the carbonyl-like compound. Preferably, the carboxylic acid is added in a total of 10-40% stoichiometric excess. More preferably, the carboxylic acid is added in 15-25% stoichiometric excess.

The esterification process of the present invention may also include one or more of the following steps: removal of excess reagent by nitrogen or steam stripping; addition of adsorbents such as alumina, silica gel, activated carbon, clay and/or filter aid to the reaction mixture following esterification before further treatment. In certain cases adsorbent treatment may occur later in the process, following stripping, and in still other cases the adsorbent step may be eliminated from the process altogether. Addition of water and base to simultaneously neutralize the residual organic acids and hydrolyze the catalyst (if present); filtration of solids from the ester mixture containing the bulk of the excess reagent (acid or alcohol) used in the esterification process; removal of the excess reagent from the ester mixture by, for example steam or nitrogen stripping under vacuum and recycling of the excess reagent to the reaction vessel; and, removing solids from the stripped ester in a final filtration, may also be included in the process of the present invention.

Further productivity benefits may be achieved in esterification processes that produce more than one ester product, and which on a regular basis have to switch from one product to another. The conventional method is to shut down and empty the unit and clean the equipment by e.g. a water wash. This introduces a significant amount of down time, and possibly generates substantial volumes of waste water that needs to be disposed of An alternative is a dry changeover, thus eliminating the use of water, but which because of grade cross-contamination typically produces a certain volume of mixed grade product material, which is generally not compliant with any of the individual product grade specifications and therefore may need to be downgraded to a lower sensitivity end-use or be reworked.

Our preferred method is to apply a flying grade switch procedure, here exemplified in the production of phthalate esters. The objective of this flying grade-switch is to minimize the production loss and the grade cross-contamination, while switching from one alcohol feed grade to another. The flying grade-switch is executed by maximizing the feed rate to the finishing unit, while having at the same time a minimum liquid holdup. As a preparation for a flying grade-switch, exemplified here in a batch reactor unit combined with a continuous finishing unit, all drum levels are gradually reduced to the minimum level required to keep the esterification unit pumps and mixers running This also allows for a continued operation of the solids addition systems. Furthermore, all precoat filters are preferably switched just before the completion of the first batch of the new grade. The precoat drum, where the filter precoat material is mixed with liquid before transfer to the filter system, is preferably emptied into the filtration feed drum prior to the grade switch.

The alcohol feed line and the alcohol feed drum are preferably emptied into the last reactor batch of the old grade. In tankage, the feed alcohol and recycle alcohol tanks are then switched over to the new grade, and the reactor feed drum is filled with the new alcohol grade. The new grade recipe is loaded into the reactor process control system. The reactor section is now ready for the production of the first batch of the new grade.

After dumping the last batch of crude ester of the old grade, the feed drum of the continuous finishing unit is emptied to reach about 10% drum level just before dumping the first batch of the new grade into that drum. At this time, the adsorbent and filter aid solids addition to the feed drum of the secondary filtration unit, which is typically located downstream of the excess alcohol stripper tower, is preferably also already stopped, and this preferably when the drum content has first been reduced to its minimum level. After dumping the first batch of the new grade into the finishing feed drum, the hydrolysis water ratios are typically adjusted to the requirements of the new grade.

After feeding 45% of the total volume of new crude ester, required for flushing out the old grade from the continuous finishing section, the liquid circulation flows over the secondary filtration unit and its dosing system are also stopped, while the stripper feed preheater temperature is adjusted to the new conditions. When reaching 90% of the required flushing volume, the operator starts checking the density of the plasticizer rundown product. At 100% of the flushing volume, the recycle alcohol rundown from the stripper is switched from the old grade tank to the new grade tank.

After measuring the target plasticizer density for the new grade, the rundown of the unit is switched from the old grade to the new grade tank. The circulation flows over the secondary filtration unit and its dosing system are restarted. The filtration drum levels are reestablished followed by restarting the mixers and the adsorbent and filter aid dosing. All other drum levels are then returned to their target values.

Esterification catalysts that may be used include acid catalysts and organometallic catalysts. Organometallic esterification catalysts are preferred and include titanium, zirconium and tin catalysts such as titanium, zirconium and tin alkoxides, carboxylates and chelates. See U.S. Pat. No. 3,056,818 (Werber) which issued on Oct. 2, 1962, and which is incorporated herein by reference. Titanium alkoxides are preferred.

Typical titanium alkoxides which can be used as catalysts include tetramethyl titanates, tetraethyl titanates, tetrapropyl titanates, tetra-isopropyl titanates, tetrabutyl titanates, tetrapentyl titanates, tetrahexyl titanates, tetraheptyl titanates, tetra-octyl titanates, tetranonyl titanates, tetradecyl titanates including tetra-2-propylheptyl titanate, tetradodecyl titanates, tetrahexadecyl titanates, tetra-octadecyl titanates, tetraphenyl titanates, and mixtures thereof. The alkoxy groups on the titanium atom can all be the same or they can be different, and their alkyl chains may be normal and/or branched, or mixtures thereof. The tin or zirconium counterparts of the above alcoholates can be substituted in whole or in part as catalysts. Tetra-isopropyl titanate (TIPT) is very suitable. Tetra-isooctyl titanates (TIOT) are even more preferred.

Polyol (i.e., polyhydroxy) compounds are represented by the general formula:

$R(OH)_n$.

wherein R is an alkyl, alkenyl, or aralkyl hydrocarbyl group and n is at least 2, and can be used in place of the mono alcohols when polyol esters are desired. The hydrocarbyl group may contain from about 2 to 20 or more carbon atoms, and the hydrocarbyl group may also contain substituents such as chlorine, nitrogen, and/or oxygen atoms. The polyhydroxy compounds generally will contain from about 2 to 10 hydroxy groups and more preferably from about 2 to 6 hydroxy groups. The polyhydroxy compound may contain one or more oxyalkylene groups and, thus, the polyhydroxy compounds include compounds such as polyetherpolyols. The number of carbon atoms and number of hydroxy groups contained in the polyhydroxy compound used to form the carboxylic esters may vary over a wide range.

The following polyols are particularly useful: neopentyl glycol, 2,2-dimethylol butane, trimethylol ethane, trimethylol propane, trimethylol butane, mono and technical grade (i.e., 88% mono, 10% di and 1-2% tri) pentaerythritol, dipentaerythritol, ethylene glycol, propylene glycol, butane diol and polyalkylene glycols (e.g., tetraethylene glycol, polyethylene glycols, polypropylene glycols, polybutylene glycols, etc., and blends thereof such as a polymerized mixture of ethylene glycol and propylene glycol).

The method according to the present invention is capable of forming plasticizer esters, such as, benzoates, cyclohexanoates and cyclohexanoic dicarboxylic esters, phthalates, adipates, and trimellitates, from $C_4$ to $C_{15}$ alcohols, preferably $C_6$ to $C_{13}$. Preferred alcohols include hexanol, heptanol, isoheptanol, 2 ethyl hexanol, nonanol, isononanol and mixtures of branched chain nonanols, linear and branched chain decanols, including 2-propyl-heptanol, normal and/or branched undecanol and tridecanol. Because of the increase in the rate of reaction, in accordance with this invention, the process is particularly useful in esterifications catalyzed by titanium, zirconium, or tin organometallic catalysts.

The method of the present invention is also useful in forming polyol esters, such as, neopolyol esters, from polyols and excess fatty acids. The polyol or polyol mixture is preferably technical grade pentaerythritol (PE), trimethylolpropane (TMP), and neopentylglycol, each of which can be admixed with monopentaerythritol and/or trimethylol propane or other neopolyols. The preferred acid component is typically a mixture of straight chain acids having five to ten carbon atoms, or a branched chain acid having from five to eighteen carbon atoms, preferably five to nine carbon atoms, namely isopentanoic, 2-methylpentanoic, 2-methylhexanoic, 2-ethylpentanoic, 2-ethylhexanoic, 3,5,5-trimethylhexanoic, 2,4-dimethyl heptanoic, 2-propyl-heptanoic acids or mixtures thereof. Also mixtures of normal and branched acids may be used. Generally, the acids are monocarboxylic acids. Suitable straight chain acids include, but are not limited to, valeric acid, enanthic acid, caprylic acid, pelargonic acid, and capric acid.

The branched chain acid may be iso-$C_5$, iso-$C_7$, iso-$C_8$, or iso-$C_9$. Preferably, the branched chain acid used is the iso-$C_7$ acid. Another preferred branched acid is 3,5,5-trimethylhexanoic acid derived from the oxonation/oxidation of di-isobutylene. Still another preferred branched acid is oxo-octanoic acid derived from the oxonation/oxidation of mixed heptenes. Yet another preferred acid is isopentanoic acid, which is typically a mixture of normal and branched C5 acids.

In the reaction used to form polyol esters, the acid mixture is typically present in a stoichiometric excess of about 10 to 50 mole percent or more, for the amount of polyol used and the amount of alcohol functions that is desired to be esterified. The excess acid is used to force the reaction to completion. The composition of the feed acid is adjusted so as to provide the desired composition of product ester. After the reaction is complete, the excess acid is removed by stripping and additional finishing.

DESCRIPTION OF THE DRAWINGS

The drawings are included to further illustrate the invention.

The present invention is illustrated for a phthalate ester production by reference to the accompanying drawing in which FIG. 1 shows a reactor (1) provided with a mixer (2) and a heating element (3). The apparatus is provided with means for alcohol recovery which includes a packed tower or column (4) disposed above reaction vessel (1). Packed tower (4) preferably includes one or two stages with low pressure drop stainless steel packing (loose or structured). The vapours from reaction vessel (1) pass up tower (4) and contact with alcohol from the overhead collection drum (5). Collection drum (5) is a three phase or settling drum which allows the alcohol and water to separate into two liquid phases. Drum (5) operates on phase level control. That is, the alcohol phase overflows weir (6) and is either recycled to the reaction vessel (1) or sent to tankage via conduit (7). The water phase is drawn off from the bottom through conduit (8) and may optionally be recycled to the hydrolysis step. These liquids may flow under gravity, or may be pumped. Vapour is drawn overhead via conduit (9), condensed and the condensates may also be recycled. The apparatus is provided with a nitrogen supply (10), preferably through a sparger ring in the bottom of the reaction vessel (1), and this nitrogen supply may be used to control the pressure in the reactor. Another nitrogen supply may be provided close to the condensor (11), where it is more effective in impairing condensation and reflux when this is undesired.

The water by-product (8) may also be discarded. It contains dissolved organics, primarily alcohols. Preferably it is therefore discarded via a biological oxidation (BIOX) unit to reduce its biological oxygen demand (BOD). In case a lighter alcohol titanate, such as TIPT, is used as catalyst, this water may contain significant amounts of the light alcohol, such as isopropanol. Heavier alcohol titanates, such as TIOT, are preferred as catalysts so that the BOD load of this water is low, and its load on the BIOX unit is reduced.

Figure 1:
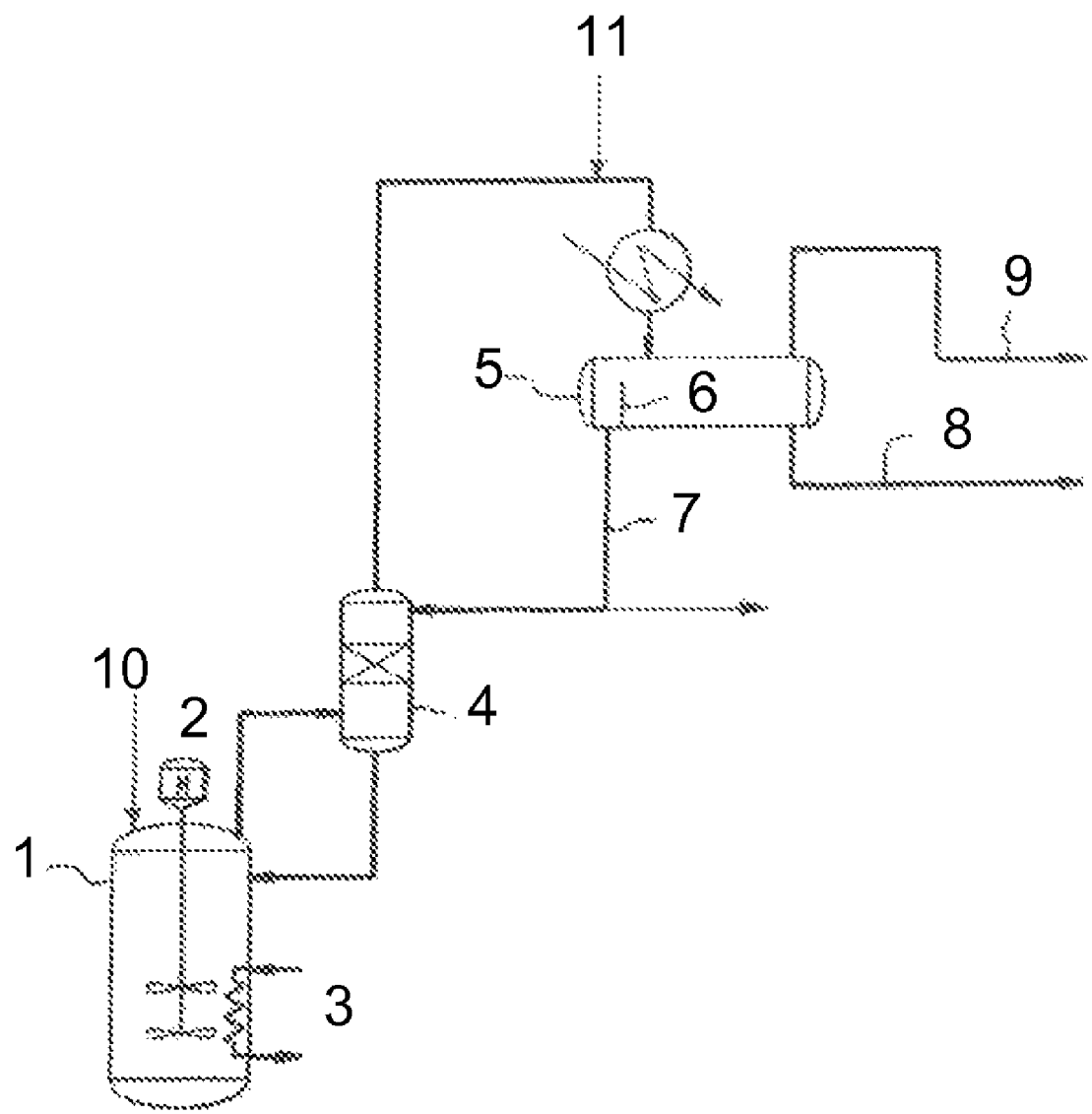
FIG. 1 shows a flow sheet of a preferred esterification reactor vessel setup, suitable for the process of the present invention.
Figure 2:
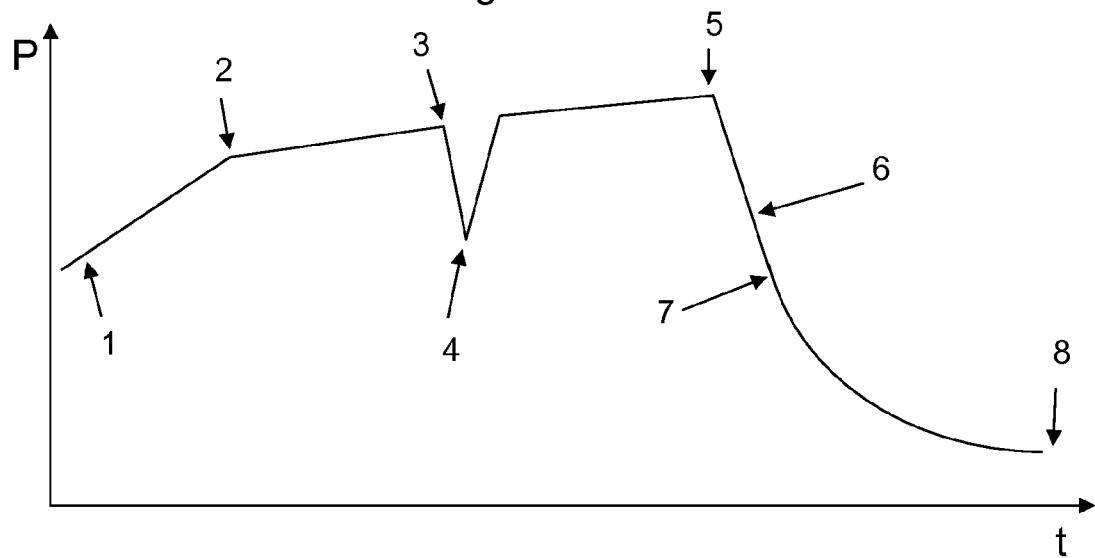
FIGS. 2 and 3 show two alternative esterification reaction pressure profiles over time that are according to the invention.
Figure 3:
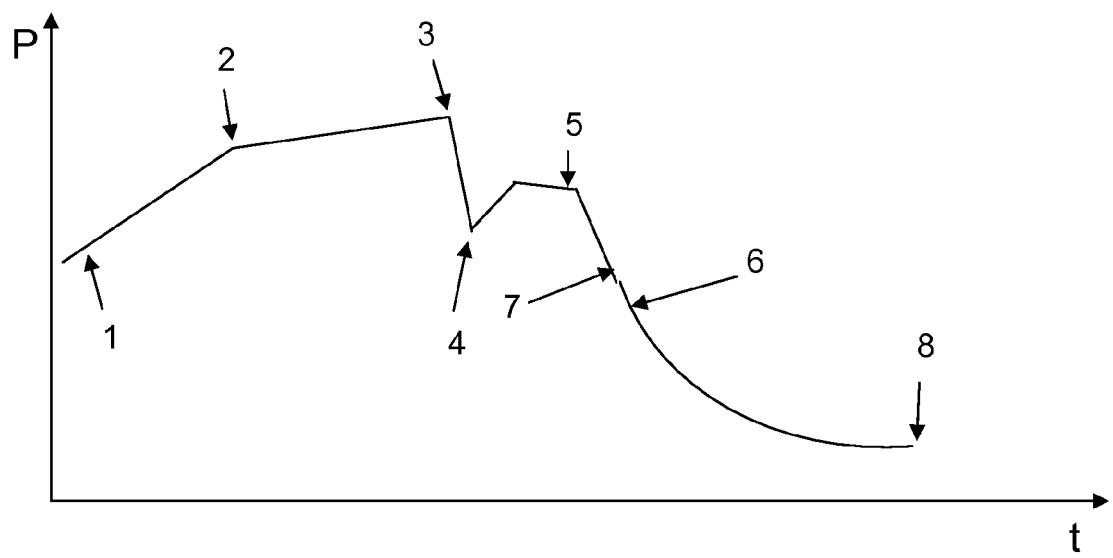

FIGS. 2 and 3 illustrate two alternatives of typical reaction vessel pressure profiles over time according to the present invention, in which the temperature and pressure of the vessel and its content is raised (1) to the predetermined mixture temperature of 180° C., when titanate catalyst is added (2) and the temperature is raised further to the minimum desired esterification reaction temperature of 210° C. (5) whilst at least retaining the elevated pressure, but preferably increasing it further (5). Along this path, preferably when condensibles reach the overhead condensor and a sudden drop in pressure (3) may be experienced, nitrogen is injected (4) to either restore the pressure (as in FIG. 2) or keep it at a level sufficient to control reflux at a relatively low rate (as in FIG. 3), so that the reaction temperature may continue to increase as fast as the heat input allows. Once the minimum desired esterification reaction temperature is reached (5), the pressure is relaxed by venting to atmospheric pressure and/or pulling vacuum (7) while the temperature may still increase further to the maximum desired esterification reaction temperature of 220° C. (6), and the pressure may be reduced further below atmospheric by commissioning the vacuum system, until finally the reaction is stopped when the desired conversion is reached (8). Stopping the reaction is conventionally achieved by stopping the heat input, typically combined with breaking the vacuum in the reactor and/or in the overhead system. Up to the moment that the minimum reaction temperature is reached (5), the target is to maximise use of the available heat input to heating up the reaction liquid. After that moment, the target is to maximise use of the available heat input for reflux (hence for water removal from the reactor liquid) while at least maintaining the reaction temperature.

Having now fully described this invention, it will be appreciated by those skilled in the art that the invention can be performed within a wide range of parameters within what is claimed, without departing from the spirit and scope of the invention.

The invention claimed is:

1. A process for the catalysed esterification of reactants comprising at least one of an acid or an acid anhydride, and an alcohol, to produce at least one of a plasticizer ester for polyvinylchloride (PVC) from a $C_4$ to $C_{15}$ monohydric alcohol or a polyol ester from a polyol and a fatty acid, which process comprises a batch reaction sequence that comprises:
   (i) providing a mixture of the at least one of an acid or an acid anhydride with the alcohol at an initial temperature, wherein said initial temperature is from 135° C. to 180° C., in a reaction vessel,
   (ii) raising the temperature of the mixture to a desired esterification reaction temperature, wherein said desired esterification reaction temperature is from 210° C. to 230° C., to effect esterification, and
   (iii) boiling off water by-product produced in the esterification reaction, wherein the pressure in the reaction vessel is elevated as the temperature of the mixture is raised during at least the initial phase of raising the temperature of the mixture, thereby reducing reactant vaporisation, and an esterification catalyst is introduced into the mixture at a predetermined mixture temperature, wherein said predetermined mixture temperature is from 175° C. to 220° C., that is below the desired esterification reaction temperature and above the initial temperature of the mixture.

2. The process according to claim 1 in which the pressure in the reactor vessel is maintained at an elevated level at least until the esterification catalyst is added.

3. The process according to claim 1 in which the esterification catalyst is a titanium catalyst.

4. The process according to claim 1 in which, after the esterification catalyst is added, the temperature is further increased to the desired esterification reaction temperature and the pressure is at least maintained at the same level.

5. The process according to claim 1 wherein after the desired esterification reaction temperature is reached, the reactor pressure is reduced while at least maintaining the reaction temperature, whereby preferably the reactor pressure is reduced to within the range of 26.1 psia to 4.4 psia (180 kPa to 30 kPa) (1800 mbara to 300 mbara) within 100 minutes of the addition of the esterification catalyst.

6. The process according to claim 1 in which an overhead system is provided to the reaction vessel, to condense and reflux vaporised reactants to the reaction vessel, and reflux conditions are established once the desired esterification reaction temperature has been reached.

7. The process according to claim 6, wherein the reflux is stopped at least 2 minutes before the termination of the esterification reaction.

8. The process according to claim 1 comprising:
   (i) adding heated alcohol at a temperature in the range 100° C. to 160° C. to a reaction vessel blanketed with an inert gas;
   (ii) adding to the heated alcohol in the vessel the at least one of an acid or acid anhydride;
   (iii) heating the mixture in the reaction vessel to a predetermined mixture temperature in the range of 180° C. to 220° C., thereby elevating the pressure in the vessel;
   (iv) introducing an esterification catalyst at the predetermined mixture temperature whilst maintaining an elevated pressure;

(v) raising the temperature further to the minimum desired esterification reaction temperature, whilst maintaining an elevated pressure; and (vi) then reducing the pressure to at most atmospheric.

9. The process according to claim 8 in which the temperature is maintained above the minimum desired esterification reaction temperature until the esterification reaction is complete.

10. The process according to claim 8 in which a reflux system is connected to the reaction vessel, and the reflux system is activated following introduction of the esterification catalyst.

11. The process according to claim 10 in which additional inert gas is introduced to compensate for any pressure drop due to the activation of the reflux system.

12. The process according to claim 11 in which the additional inert gas is introduced into the reaction vessel.

13. The process according to claim 11 in which the reflux system comprises a condenser and the additional inert gas is introduced into the condenser.

14. The process according to claim 1 in which the pressure of the reaction vessel is adjusted during the course of the esterification reaction to ensure continuous vaporisation and removal of water.

15. The process according to claim 1 for the production of a phthalate di-ester, further comprising hydrogenating the phthalate di-ester to produce the corresponding di-alkyl cyclohexanoate di-ester.

16. The process according to claim 6, whereby the reflux is flashed and flashed liquid is used as reflux to the esterification reaction.

17. The process according to claim 16 wherein the flashed liquid reflux is dried in a reflux drier column before it is returned to the esterification reaction.

18. The process according to claim 6, whereby the reflux is dried in a reflux drier column before it is returned to the esterification reaction.

* * * * *